US00PP25156P3

(12) United States Plant Patent
Freyre

(10) Patent No.: US PP25,156 P3
(45) Date of Patent: Dec. 9, 2014

(54) ***RUELLIA* PLANT NAMED 'R10-108'**

(50) Latin Name: *Ruellia simplex*
Varietal Denomination: R10-108

(75) Inventor: Rosanna Freyre, Gainesville, FL (US)

(73) Assignee: Florida Foundation Seed Producers, Inc., Marianna, FL (US)

( * ) Notice: Subject to any disclaimer, the term of this patent is extended or adjusted under 35 U.S.C. 154(b) by 271 days.

(21) Appl. No.: 13/507,162

(22) Filed: Jun. 8, 2012

(65) Prior Publication Data

US 2013/0333083 P1 Dec. 12, 2013

(51) Int. Cl.
*A01H 5/00* (2006.01)

(52) U.S. Cl.
USPC ..... Plt./263.1

(58) Field of Classification Search
USPC ..... Plt./263.1, 226
See application file for complete search history.

(56) References Cited

U.S. PATENT DOCUMENTS

PP10,841 P 3/1999 Grant et al.

OTHER PUBLICATIONS

Freyre et al., "Breeding and evaluating for landscape performance and fruitlessness in Mexican petunia (*Ruellia,* Acanthaceae)," *HortScience,* 47:1245-1251, 2012.
Freyre et al., "Fruitless *Ruellia simplex* R10-102 ('Mayan Purple') and R10-108 ('Mayan White')," *HortScience,* 47(12):1808-1814, 2012.

*Primary Examiner* — Kent L Bell
(74) *Attorney, Agent, or Firm* — Dentons US LLP

(57) ABSTRACT

'R10-108' is a new *Ruellia* plant distinguished by having excellent landscape performance, and flowering, white flowers, and no fruiting, as disclosed.

2 Drawing Sheets

STATEMENT REGARDING FEDERALLY SPONSORED RESEARCH

The U.S. government has certain rights in this invention, pursuant to TSTAR Grant No. 00093296 awarded by the U.S. Department of Agriculture.

Latin name of the genus and species of the plant claimed: *Ruellia simplex.*

Variety denomination: 'R10-108'.

BACKGROUND OF THE INVENTION

The present invention relates to a new and distinct variety of *Ruellia*, botanically known as *Ruellia simplex*, and hereinafter referred to by the name 'R10-108'.

'R10-108' is a tetraploid individual obtained from manual hybridization conducted in Gainesville, Fla. in September 2010, between 69-1 and RU64. 69-1 is a tetraploid breeding line, obtained as a vegetative propagule from RU63-69. RU63 is a tall, diploid white-flowering breeding line obtained in 2008 as an $F_2$ from the cross of diploid purple-flowering wild *R. simplex* and diploid dwarf variety 'Katie White'. RU63-69 is a tetraploid white-flowering individual obtained by treating the apical meristem of a seedling of RU63 with three applications (every 12 hours) of a 25 μM oryzalin solution in December 2008. RU64 is an $F_2$ tetraploid white-flowering individual obtained from a cross between 'Snow White' and RUE1-1 (a purple-flowering tetraploid South American accession of *R. simplex.*

'R10-108' has been reproduced asexually for over one year through vegetative cuttings and has been shown to retain its distinctive characteristics through successive asexual propagations. The first asexual propagation of 'R10-102' was done by tip cuttings in Gainesville, Fla. 32611 in April 2011.

'R10-108' has not been made publicly available more than one year prior to the filing date of this application.

BRIEF SUMMARY OF THE INVENTION

The following are the most outstanding and distinguishing characteristics of 'R10-108' when grown under normal horticultural practices in Northwestern, North Central, and Southeastern Florida, USA:

1. Excellent growth in both full sun and partial shade environments.
2. Prolific flowering throughout the flowering season.
3. Large white flowers.
4. No fruit production.

BRIEF DESCRIPTION OF THE DRAWINGS

The accompanying photographs illustrate the form and foliage of the new *Ruellia* variety. The colors shown are as true as can be reasonably obtained by conventional photographic procedures.

DETAILED BOTANICAL DESCRIPTION

Figure 1:
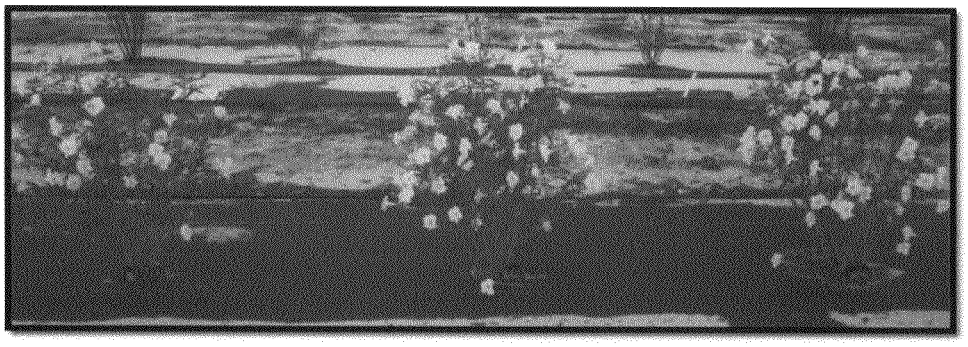
FIG. 1. Shows a plot of three plants of 'R10-108' taken on Aug. 29, 2011. The photograph was taken of 21-week-old plants grown in ground beds with drip irrigation in Citra, Fla. (North Central Florida, 29.4° N, 82.2° W, AHS heat zone 10).
Figure 2:
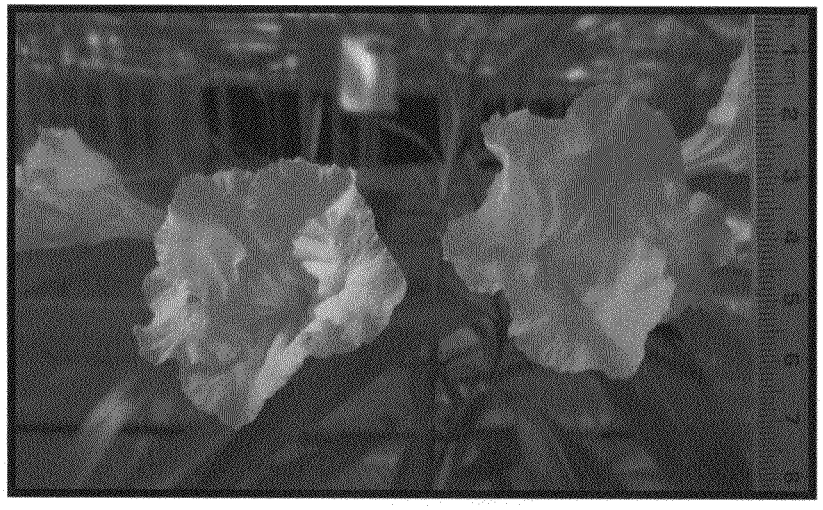
FIG. 2. Shows a close-up view of flowers of 'R10-108' on an 8-week-old greenhouse plant, taken on May 8, 2012.

The following detailed description sets forth the distinctive characteristics of 'R10-108'. The detailed description was taken on May 8, 2012, 8 weeks after vegetative propagation from greenhouse-grown stock plants. Measurements are the mean values from 3 individual clones propagated on Mar. 12, 2012 and greenhouse-grown in 6" Azalea pots using Fafard 2P mix (60% Canadian peat moss, 40% perlite) and fertigation at 150 ppm N.

Color references are to The R.H.S. Colour Chart of The Royal Horticultural Society of London (R.H.S.), 2001 Edition.

Phenotypic Description of *Ruellia simplex* (Variety 'R10-108')

Classification:

*Family*.—Acanthaceae.

*Botanical*.—*Ruellia simplex* hybrid.

*Common name*.—*Ruellia*, Mexican Petunia.

*Variety name*.—'R10-108'.

*Plant description*.—Form: Erect. Habit: Clumping. Height (from top of soil): 62.7 cm. Width (horizontal plant diameter): 60.0 cm.

Propagation:

*Type cuttings*.—Vegetative meristems having at least 2 nodes.

*Time to initiate roots*.—4 to 6 days.

*Time to produce a rooted cutting*.—7 to 10 days.

*Root habit*.—Adventitious (fibrous).

*Root description*.—Callus forms in 3 to 4 days; roots initiate in 5 to 8 days and become a highly branched cutting in 14 to 21 days.

Branches:

*Quantity per plant*.—5 to 7 per plant (with no pinching).

*Branch color*.—RHS 143A (Green).

*Texture*.—Smooth.

*Pubescence*.—Slightly tomentose, especially at nodes.

*Stem description*.—Round to square shaped stem, 4.9 cm in diameter at the soil line.

*Branch diameter*.—2.6 cm at the base of a 30 cm long branch.

*Branch length*.—30 cm.

*Internode length*.—9.3 cm.

*Anthocyanin*.—N/A.

Leaves:

*Quantity of leaves per branch*.—8 to 10.

*Arrangement*.—Decussate (opposite pairs).

*Fragrance*.—N/A.

*Shape*.—Lanceolate to elliptic.

*Length*.—23.8 cm.

*Width*.—3.8 cm.

*Apex*.—Narrowly Acute.

*Base*.—Attenuate.

*Margin*.—Entire.

*Leaf texture* (*both surfaces*).—Slightly coriaceous.

*Pubescence color* (*both surfaces*).—N/A.

*Venation color*.—Upper surface: RHS 139A (Green). Lower surface: RHS 137C (Green).

*Venation pattern*.—Pinnate.

*Color, mature and immature leaf*.—Upper surface: RHS 139A (Green). Lower surface: RHS 137C (Green).

*Petiole length*.—1.8 cm to 2.0 cm.

*Petiole diameter*.—0.4 cm.

*Petiole color*.—RHS 143A (Green).

Flowers and seeds:

*Flower* (*if present*).—Arrangement: Axillary in solitary or several-flowered cyme. Aspect: Actinomorphic corolla with 5 rounded petals; funnel form. Flowering habit (length of flowering season): May to October (N. FL). Number of inflorescences per plant: 10-12 simple cymes with 40-65 flowers+total buds. Length of inflorescence: 12-15 cm. Width of inflorescence: 10-15 cm. Fragrance: Very mild and slightly sweet. Lastingness of individual bloom: 1 day. Rate of opening: Daily.

*Flower bud*.—Shape: Elliptic. Length: 2.0 cm. Diameter: 1.2 cm. Color: RHS 143A (Green). Texture: Glandular with trichomes.

*Corolla*.—Arrangement: Actinomorphic salverform (funnel form). Length: 6.5 to 7.5 cm. Width: 5.4 to 6.7 cm. Number of petals per flower: 5. Petal Length: 2.0 to 2.5 cm. Petal Width: 2.5 cm at widest point. Apex: rounded and undulated. Color: Upper surface: RHS 155C (White). Lower surface: RHS 155C (White). Throat: RHS 155C (White).

*Banner*.—Not present.

*Margin*.—Texture (both surfaces): Smooth. Color: Upper surface: RHS 155C (White). Lower surface: RHS 155C (White).

*Keel*.—Not present.

*Calyx*.—Number of sepals per flower: 5. Length: 2.0 cm. Diameter: 1.5 cm. Apex: Narrowly Acute. Base: Fused. Margin: Smooth. Texture (both surfaces): Smooth to glandular (see below). Pubescence (present or absent): Present (Glandular trichomes). Sepal color: Upper surface: RHS 143A (Green). Lower surface: RHS 143A (Green).

*Pedicels*.—Angle: 15-25°. Length: 0.8 cm. Diameter: 0.7 cm. Texture: Smooth to glandular. Color: RHS 143A (Green).

*Reproductive organs*.—Stamens: Present. Number: 4 anthers with stamens fused at base to corolla. Filament: 4 (fused). Color: RHS 155D (White). Length: 2 at 2.0 cm, and 2 at 1.3 cm. Diameter: 0.2 cm. Anther color: N/A. Pollen amount: Moderate (not viable). Pollen color: RHS 155D (White). Pistils: Number/flower: 1. Pistil length: 3.2 cm. Stigma: Present. Color: RHS 155D (White). Shape: Bilabial and slightly recurved. Length: 0.2 cm. Diameter: 0.2 cm. Style: Color: RHS 155D (White). Length: 3 cm. Diameter: 0.2 cm. Ovary: Hypogenous. Shape: Elliptic. Color: RHS 143A (Green).

Fruit/seed set: None observed.

Disease and insect resistance: Disease and insect resistance is typical of the species.

Comparison with Parental Lines and Known Variety

Compared to the female parent 69-1, 'R10-108' has a more compact and full growth habit, less-rounded leaves, and no fruiting. Compared to the male parent RU64, 'R10-108' has a more compact and full growth habit, more elliptical leaves, and no fruiting.

For comparison of 'R10-108' with the known variety *Ruellia simplex* 'Snow White', measurements were done on 27 plants per variety that were 20-22 weeks old, grown in the field in 2011 in North (Quincy), Central (Citra), and Southeastern (Fort Pierce) FL, and then averaged. Both 'R10-108' and *Ruellia simplex* 'Snow White' measured an average of 88 cm in height. 'R10-108' had an average width of 84 cm, as compared to 'Snow White' with 67 cm. The average corolla diameter of 'R10-108' ranged from 5.5 to 6.7 cm, compared to 5.2 to 6 cm in 'Snow White'. The average landscape performance rating values (evaluated monthly from weeks 0 to 24 at three sites, based on 27 plants) were 4.4 and 3.1 for 'R10-108' and 'Snow White', respectively, where landscape performance was rated on a scale from 1-5, with 1=very poor quality, not acceptable, severe leaf necrosis or chlorosis, and poor form; 2=poor quality, not acceptable, large areas of necrosis or chlorosis, and poor form; 3=acceptable quality, and somewhat desirable form and color; 4=very good quality, very acceptable, and desirable color and form; and 5=excellent quality, perfect condition, and premium color and form. The average flowering rating values (evaluated monthly from weeks 0 to 24 at three sites, based on 27 plants) were 4 and 2.9 for 'R10-108' and 'Snow White', respectively, where flowering was rated on a scale from 1-5, with 1=no flowers or buds; 2=buds but no open flowers; 3=1-10 open flowers; 4=11-20 open flowers; and 5=more than 20 open flowers per plant. The average fruiting rating values (evaluated monthly from weeks 0 to 24 at three sites, based on 27 plants) were 4.9 and 3.7 for 'R10-108' and 'Snow White', respectively, where 1=more than 50 fruits; 2=21-50 fruits; 3=11-20 fruits; 4=1-10 fruits; and 5=no fruits. A few small fruits were noted on 'R10-108' in the field (from open pollination), but it was observed that they aborted before maturation.

What is claimed is:

1. A new and distinct variety of *Ruellia* plant as shown and described herein.

* * * * *